(12) United States Patent
Righettini et al.

(10) Patent No.: US 9,841,363 B2
(45) Date of Patent: Dec. 12, 2017

(54) MODULAR EQUIPMENT FOR AUTOMATICALLY DETERMINING FEATURES OF ELONGATED TEXTILE SAMPLES OF THE YARNS, THREADS, TAPES TYPE AND THE LIKE

(71) Applicant: MESDAN S.p.A., Puegnago Del Garda (IT)

(72) Inventors: Paolo Righettini, Toscolano Maderno (IT); Andrea Ginammi, Mapello (IT)

(73) Assignee: MESDAN S.p.A., Puegnago del Garda (IT)

( * ) Notice: Subject to any disclaimer, the term of this patent is extended or adjusted under 35 U.S.C. 154(b) by 0 days.

(21) Appl. No.: 15/295,228

(22) Filed: Oct. 17, 2016

(65) Prior Publication Data

US 2017/0108417 A1    Apr. 20, 2017

(30) Foreign Application Priority Data

Oct. 20, 2015   (IT) .......................... 102015000063323

(51) Int. Cl.
  *G01N 3/08*   (2006.01)
  *G01N 33/36*   (2006.01)

(52) U.S. Cl.
  CPC ............... *G01N 3/08* (2013.01); *G01N 33/36* (2013.01); *G01N 33/365* (2013.01)

(58) Field of Classification Search
  CPC ......... G01N 3/08; G01N 33/36; G01N 33/365

(Continued)

(56) References Cited

U.S. PATENT DOCUMENTS

| | | | |
|---|---|---|---|
| 3,805,607 A | | 4/1974 | Heusser |
| 4,319,493 A | * | 3/1982 | Roos ..................... G01N 3/08 |
| | | | 73/828 |

(Continued)

FOREIGN PATENT DOCUMENTS

CH      708 393 A2    1/2015

OTHER PUBLICATIONS

Italian Search Report dated Jun. 22, 2016 in Italian Application UB20155052 filed on Oct. 20, 2015 ( with English Translation of Categories of Cited Documents).

(Continued)

*Primary Examiner* — Jewel V Thompson
(74) *Attorney, Agent, or Firm* — Oblon, McClelland, Maier & Neustadt, L.L.P.

(57) ABSTRACT

Modular equipment for automatically determining features of elongated textile samples is provided. The equipment includes a housing on which a loading module for loading inlet ends of textile samples to be tested is mounted, a measurement module for measuring at least feature of the textile samples, a handling device for handling the textile samples between the loading module and the measurement module, and a central unit of the programmable type for controlling and managing the loading module, the measurement module, and the handling means. The loading module includes gripping members that are arranged aligned to one another along a loading direction, a carriage that is driven in a movable manner in both translation senses along a translation direction parallel to the loading direction, and a motor associated with the carriage for operating the carriage moving along the translation direction.

12 Claims, 7 Drawing Sheets

(58) Field of Classification Search
USPC .................. 73/160, 828–831, 860, 827, 9
See application file for complete search history.

(56) References Cited

U.S. PATENT DOCUMENTS

| | | | | |
|---|---|---|---|---|
| 4,453,406 | A | * | 6/1984 | Spitzer ............. G01N 35/00029 198/456 |
| 5,050,437 | A | * | 9/1991 | Etter ..................... G01N 3/08 73/830 |
| 5,351,535 | A | | 10/1994 | Etter et al. |
| 5,842,373 | A | * | 12/1998 | Stein ..................... G01N 3/08 73/160 |
| 6,857,259 | B2 | * | 2/2005 | Wortmann ............. B65H 51/08 226/91 |
| 8,079,255 | B2 | * | 12/2011 | Schulthess ........... G01N 33/365 73/159 |

OTHER PUBLICATIONS

"Statex Evenness Tester-600", Statex Engineering, XP54975929, 2012, 1 page.

\* cited by examiner

MODULAR EQUIPMENT FOR AUTOMATICALLY DETERMINING FEATURES OF ELONGATED TEXTILE SAMPLES OF THE YARNS, THREADS, TAPES TYPE AND THE LIKE

BACKGROUND OF THE INVENTION

Field of the Invention

The present invention refers to a modular equipment for automatically determining features of elongated textile samples of the yarns, threads, tapes type and the like.

Description of the Related Art

The quality control of a yarn is of fundamental importance to control both the production processes and the subsequent treatment processes thereof.

In general, the quality control of a yarn consists in determining different structural and/or physical-mechanical features. More specifically, the yarn is the object of various tests adapted to verify the structural features thereof, like for example the linear mass (count), the number of twists, the hairiness, the linear evenness, i.e. the constancy of the structural features along the longitudinal extension thereof, and the physical-mechanical features, like for example the dynamometric features such as the elongation at break by tension, the tensile strength (i.e. the maximum stress under tension before breaking), the elastic modulus under tension and the relative stress/strain curve.

Automatic or semi-automatic devices for determining single structural or physical/mechanical features of yarns are known.

For example, automatic or semi-automatic devices for determining the linear mass (the so-called "count calculators") or the hairiness (the so-called "hairiness meters") or the linear evenness (the so-called "evenness meters") or the dynamometric features (the so-called "dynamometers") are known.

The complete characterization of the yarns requires the determination of a plurality of such features; it is thus necessary to have a corresponding plurality of such devices on each of which the tests must be carried out individually often with the assistance of an operator responsible for loading the single yarns to be tested.

The results of the various tests, moreover, must be collected, correlated and processed so as to obtain a complete definition of the single yarns to then be compared with reference standards.

This operating way requires the installation and management of various devices, is particularly laborious, complex and long and often needs the intervention or in any case the assistance of an operator.

Multi-functional automatic or semi-automatic equipments are also known, which carry out more tests, even simultaneously, on one same sample of yarn or even on samples of yarns different from one another.

Examples of such automatic or semiautomatic equipments are described in U.S. Pat. No. 8,079,255, U.S. Pat. No. 5,842,373 or U.S. Pat. No. 4,843,879. U.S. Pat. No. 4,843,879 describes an equipment provided with two measurement stations: a first station, at which there are a device for determining the count and a device for determining the linear evenness of a sample of yarn being tested, and a second station, at which there are a device for determining the torsion and/or the dynamometric features of a sample of yarn being tested. The two measurement stations can operate successively or simultaneously on one same sample of yarn or on different samples of yarn.

The equipment is fed at the inlet by a plurality of packages (reels, spools, spindles, etc.) supported by a creel; a pneumatic system draws the yarns of each package entering the equipment.

The ends of the yarns entering the equipment are arranged manually between respective gripping members, which are arranged along an arc of circumference and as a whole form a loading device.

A handling arm having three degrees of freedom and provided with a head equipped with a gripping element and with a cutting element is arranged to pick up the inlet ends of the yarns from the loading device and distribute them in the two measurement stations.

Each of the two measurement stations is controlled by a respective microprocessor so as to be able to operate independently from one another; these microprocessors are connected to a central control and processing unit for controlling and processing the data detected during the course of each test.

A suction device unthreads and evacuates the tested textile samples.

This equipment, even proving particularly advantageous, has some drawbacks inherent, in particular, to the loading and handling device for loading and handling the textile samples.

The inlet ends of the textile samples are picked up by the respective gripping members by the handler and are inserted by it into one of the testing devices following a path that is at most defined by return rollers having fixed positions; thus each textile sample follows a different path along which it is subjected to uncontrollable tension and/or friction forces that affect the single tests, as well as being able to damage or in any case alter the single sample being tested.

The cutting of the textile samples already tested is then carried out by the handler and the portion of the textile sample tested is evacuated by a common suction device. This, on the one hand, slows down the operation of the equipment and, on the other hand, makes it difficult to correctly remove the tested textile sample, which could become tangled in the various components of the equipment. Automatic or semi-automatic equipments for measuring dynamometric features are also known, which are marketed by the firm USTER Technologies AG as "Uster® Tensorapid 4" and which are provided with a loading device consisting of a plurality of gripping members for gripping the free end of a respective textile sample fed by a corresponding package (spool, reel, spindle, etc.) supported by a creel. These gripping members are supported in succession, one after the other, by a motorized belt or chain that arranges them individually and in succession at a fixed inlet device comprising guiding and return rollers, a cutting group and a suction group.

A handling arm picks up the end of the textile sample to be tested from the respective gripping members, which have been aligned in advance with the inlet device, and inserts it into the actual dynamometer making it pass through the inlet device.

In this case, the tests are carried out on one textile sample at a time. Tests on different textile samples are carried out in the same order and in the same sequence in which the textile samples are inserted in the gripping members of the loading device; such gripping members, in fact, are individually arranged, one after the other, at the inlet device.

A loading device of this kind, moreover, is not suitable for being applied on equipments capable of simultaneously carrying out two or more tests on two different samples.

BRIEF SUMMARY OF THE INVENTION

The purpose of the present invention is to avoid the drawbacks of the prior art.

In this general purpose, a particular purpose of the present invention is to provide a modular equipment for automatically determining features of elongated textile samples of the yarns, threads, tapes type and the like, which allows feeding and handling the single textile samples to be tested so as to be able to control possible pre-loads due to friction or tensile forces exerted on them and thus obtain more accurate and precise measurements.

Another purpose of the present invention is to provide a modular equipment for automatically determining features of elongated textile samples of the yarns, threads, tapes type and the like, which allows managing in a versatile manner the loading and feeding of the single textile samples to be tested and which allows even simultaneous loading and feeding of two or more textile samples, avoiding friction and pre-loads thereof.

Yet another purpose of the present invention is to provide a modular equipment for automatically determining features of elongated textile samples of the yarns, threads, tapes type and the like, which allows performing two or more measurements of structural and/or physical-mechanical features of textile samples in an integrated manner successively or simultaneously on a same sample or on different samples.

Yet another purpose of the present invention is to provide a modular and assemblable equipment for automatically determining features of elongated textile samples of the yarns, threads, tapes type and the like, which is simple, functional and cost effective.

These and other purposes are accomplished by a modular equipment for automatically determining features of elongated textile samples of the yarns, threads, tapes type and the like as defined in claim 1.

Further features are defined in the dependent claims.

BRIEF DESCRIPTION OF THE SEVERAL VIEWS OF THE DRAWINGS

The features and advantages of a modular equipment for automatically determining features of elongated textile samples of the yarns, threads, tapes type and the like according to the present invention will become clearer from the following description, given as an example and not for limiting purposes, referring to the attached schematic drawings, in which.

DETAILED DESCRIPTION OF THE INVENTION

With particular reference to the attached figures, a modular equipment for automatically determining features of elongated textile samples of the yarns, threads, tapes type and the like is wholly indicated with 100.

Figure 1:
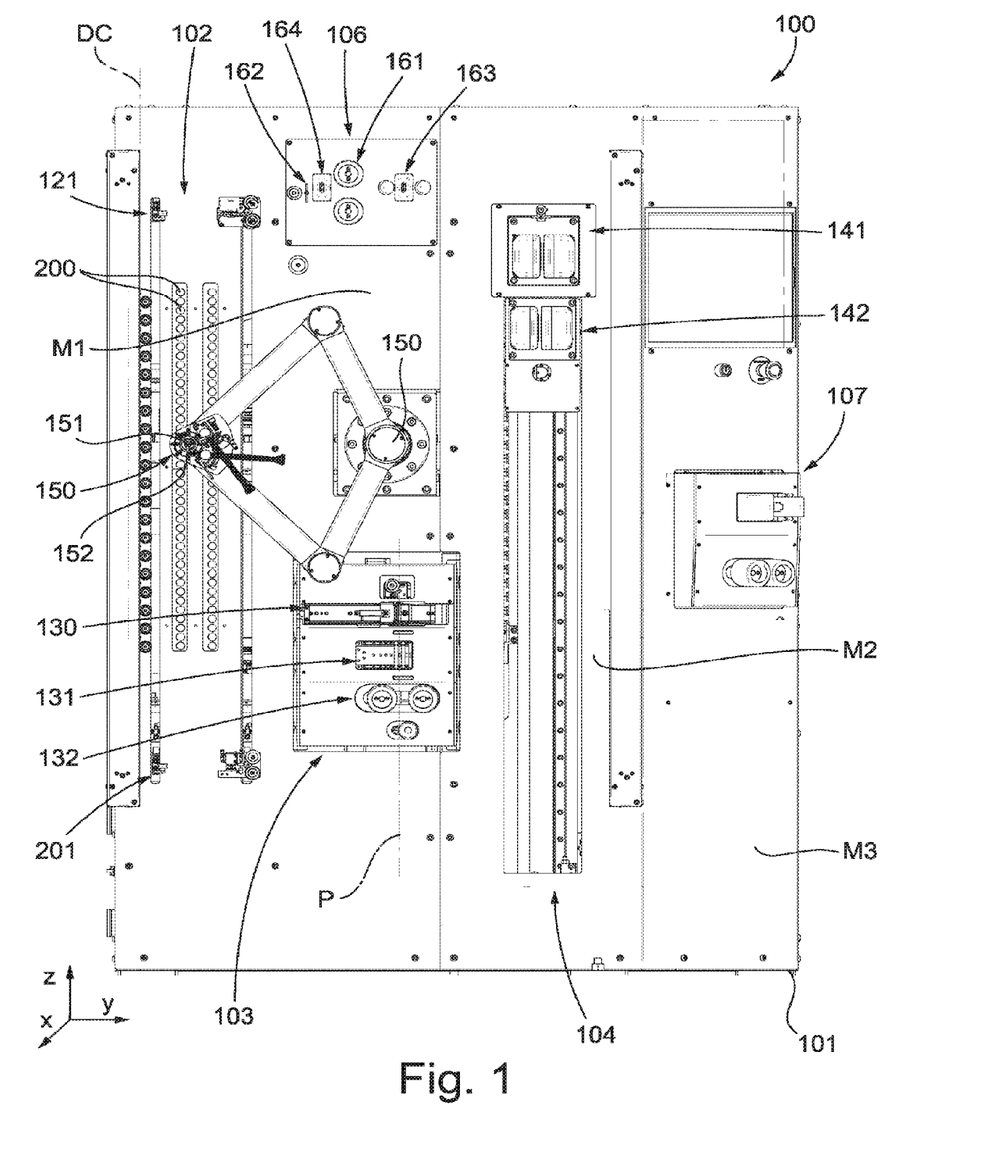
FIG. 1 is a front elevation view of a modular automatic equipment for automatically determining features of textile samples.

In the following description reference will be made to the equipment 100 considered in its usual configuration of use in which it rests on the ground and reference will be made to a Cartesian system XYZ as indicated in FIG. 1 in which the plane XY indicates the plane for resting on the ground or horizontal plane.

The equipment 100 comprises a housing 101, which the following are associated with:

a loading module 102 for loading the ends of a plurality of textile samples to be tested/characterized, each of which is wound in a corresponding feeding package of the reel, spool, spindle type or the like, supported by a creel or other equivalent support associable with the equipment 100 and not shown, at least one measurement module 103, 104 of at least one structural or physical-mechanical feature of a textile sample, handling means (i.e. handler) 105 adapted to handle the textile samples between the loading module 102 and the at least one measurement module 103, 104, a central unit of the programmable type (not shown) for managing and controlling the loading module 102, the at least one measurement module 103, 104 and the handling means 105 and for processing the measurements carried out by the at least one measurement module 103, 104.

Advantageously, the equipment 100 comprises:

at least one first measurement module 103 for measuring at least one first structural feature of the textile samples, and at least one second measurement module 104 for measuring at least one second physical-mechanical feature of the textile samples, wherein the at least one measurement module 103 and the at least one second measurement module 104 are adapted to operate successively or simultaneously on a same textile sample or on two different textile samples.

The equipment 100 can also comprise at least one third measurement module 106 for measuring a further structural feature of the textile samples and/or a fourth measurement module 107 for measuring a feature of textile samples of the rove type manually insertable into it. The various measurement modules 103, 104, 106 and 107 can also operate simultaneously and in parallel on a same or on different samples.

The first measurement module 103 is adapted to measure at least one structural feature of the textile samples selected from the evenness of the linear mass (i.e. the evenness of the count) and the hairiness, advantageously both. The first measurement module 103, therefore, comprises a device for measuring the hairiness 130 and a device for measuring the evenness (evenness of the linear mass) 131, which are arranged one above the other and substantially aligned with each other or in any case alignable along a sliding path P of the textile sample and pulling means 132 aligned or in any case alignable with the path P and which are arranged below the device for measuring the hairiness 130 and the device for measuring the evenness 131 and which are configured to make the textile sample run along the path P.

The second measurement module 104 is adapted to measure at least one physical-mechanical feature of the textile samples and, in particular, a dynamometric feature such as elongation at break by tension, tensile strength (i.e. the maximum stress under tension before breaking) and the relative stress/strain curve and, in the embodiment represented in FIG. 1, it consists of a measurement device 140 for measuring the dynamometer type that, advantageously, is of the type object of a simultaneous patent application to the same applicant and that is here entirely referred.

In general terms, the measurement device 140 comprises a pair of clamps 141, 142 arranged vertically one above of the other and the lower of which 142 is movable in translation towards and away from the upper one 141. Each clamp 141, 142 comprises a fixed jaw and a jaw movable in translation along a horizontal direction (Y axis) with respect to the fixed jaw in order to clamp and release a corresponding portion of a textile sample. The upper clamp 141 is coupled with means for detecting the force to detect the tensile force applied to the textile sample being tested, whereas the relative movement between the two clamps 141, 142 is detected directly or indirectly by transducer means.

The third measurement module 106 is adapted to measure a physical feature such as the linear mass (count) of the textile samples. The third measurement module 106 thus consists of a so-called "count calculator".

The first measurement module 103, the second measurement module 104 and the possible third and fourth measurement modules 106 and 107 are not described in detail since they are of the type known to the person skilled in the art, with the exception of the features of the embodiment of the second measurement module 104 object of the mentioned simultaneous patent application to the same applicant.

In totally general terms, the first measurement module 103 comprises a device for measuring the hairiness 130 as for example described in IT1413638 patent application and a device for measuring the evenness 131 for example of the capacitive type. In order to align the inlet opening of the device for measuring the hairiness 130 with that of the device for measuring the evenness 131, the former is supported by a slide movable upon command along a horizontal direction orthogonal to the path P.

The pulling means 132 comprise a pair of rollers rotatable in opposite senses and at controlled speeds and between which the textile sample being tested is pulled. The pulling means 132 are also supported by a slide movable upon command along a horizontal direction orthogonal to the path P to align with the inlet opening of the device for measuring the hairiness 130 and with that of the device for measuring the evenness 131.

The third measurement module 106 comprises, in general terms, own means 161 for pulling the textile sample analogous to the pulling means 132, cutting means 162 for cutting a portion of the textile sample the length of which is determined indirectly from measurements of the movement of the pulling means 161, braking means (i.e. means adapted to apply a determinable and controllable friction force to the textile sample) 163 of the textile sample, suction means 164 for sucking the cut portion of sample and weighing means housed inside the housing 101 and not shown in the attached figures.

The fourth measurement module 107 is of the known capacitive evenness meter type.

The third measurement module 106 and the first measurement module 103 are aligned one above the other in a first measuring area M1.

The second measurement module 104 is arranged in a second measuring area M2 distinct from the first measuring area M1. The possible fourth measurement module 107 is arranged in a third measuring area M3 different from the first and the second measuring areas M1 and M2 and not reached by the handling means 105.

The handling means 105 are movable between the loading module 102, the first measuring area M1 and the second measuring area M2; they are made to carry out translation and/or rotation movements about the three axes XYZ.

In the embodiment represented in the attached figures, the handling means 105 comprise an articulated quadrilateral structure movable in the vertical plane (i.e. the plane ZY as indicated in FIG. 1) and that has a cylindrical joint 150 coupled with actuator means not visible and the cylindrical joint 151 opposite with respect to it provided with a handling head 152 rotatable about the axis X and provided with gripper means for picking up and releasing the textile samples (the handling head 152 is, however, devoid of means for cutting the yarn). Advantageously, the gripper means of the handling head 152 are configured to apply a pressure proportional to the tensile strength of the textile samples being tested, said tensile strength being estimated based on the count of the textile samples themselves. This allows not to damage or break the single textile samples being tested.

Advantageously, moreover, the arms that form the articulated quadrilateral of the handling means 105 are made of carbon fiber. This allows keeping down the total weight of the handling means 105 and, therefore, limiting the inertia thereof that is the cause of imprecisions of positioning of the relative handling head 152. Moreover, making such arms of carbon fiber gives the handling means 105 high dimensional stability, to the benefit of high precision of positioning of the relative handling head 152. The handling means 105 are not described any further since they are of the type that can be immediately understood by the person skilled in the art.

Figure 2:
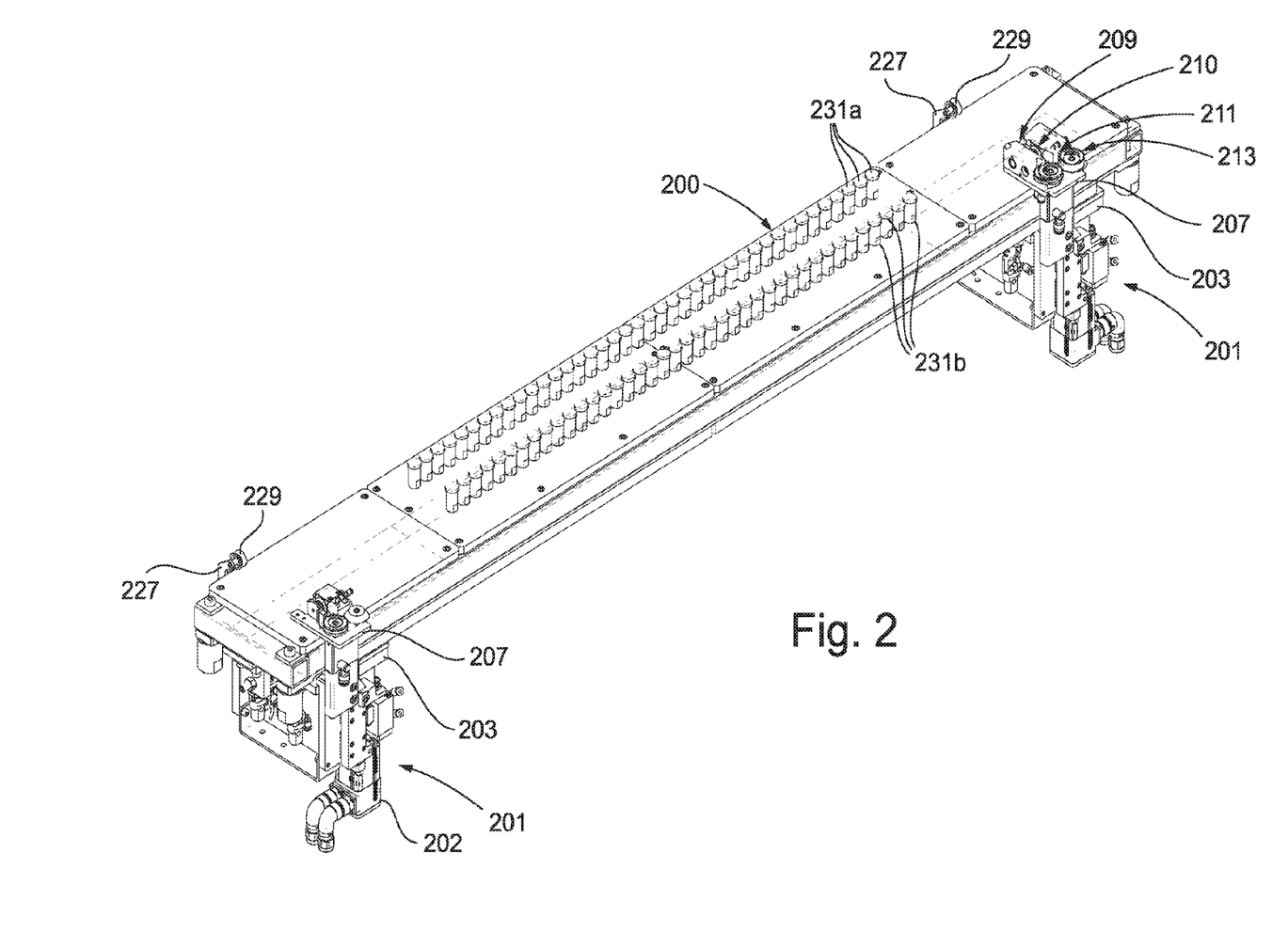
FIGS. 2 and 3 are axonometric views, from the front and rear sides respectively, of the loading module of the equipment of FIG. 1.
Figure 3:
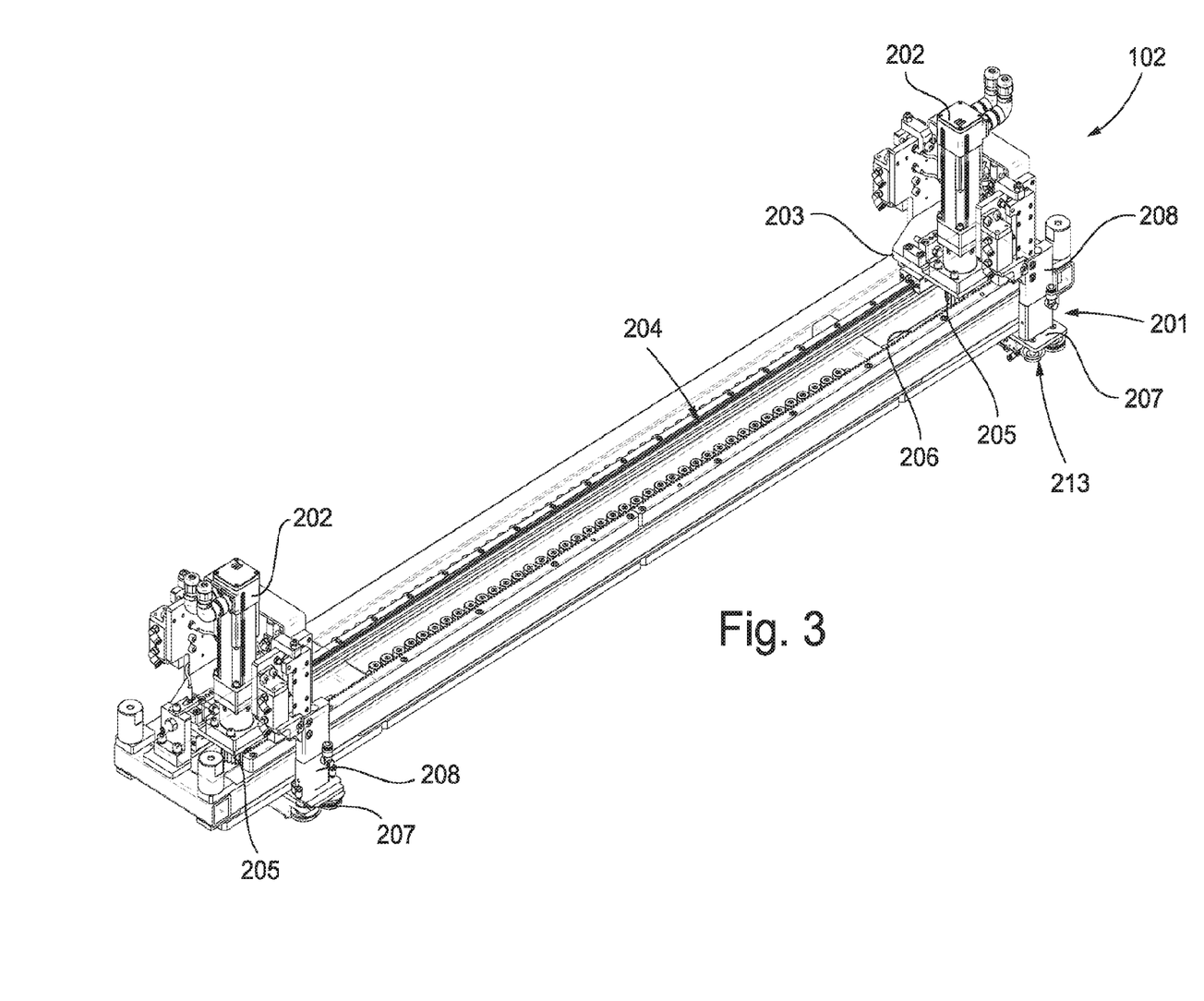

According to an aspect of the present invention, the loading module 102 comprises a plurality of gripping members 200 for locking the inlet ends of a corresponding plurality of textile samples to be tested, each of which is wound in a corresponding package of the reel, spool, spindle type or the like and supported by a creel that is not shown.

The gripping members 200 are aligned along a loading direction DC that is advantageously vertical (i.e. parallel to the axis Z) and are individually movable between a locking position and an unlocking position for locking/unlocking the inlet end of a respective textile sample.

The loading module 102 also comprises one or more, advantageously two, carriages 201, each of which is individually movable in translation in both senses along a direction parallel to the loading direction DC so as to be able to selectively align with one of the gripping members 200.

Figure 4:
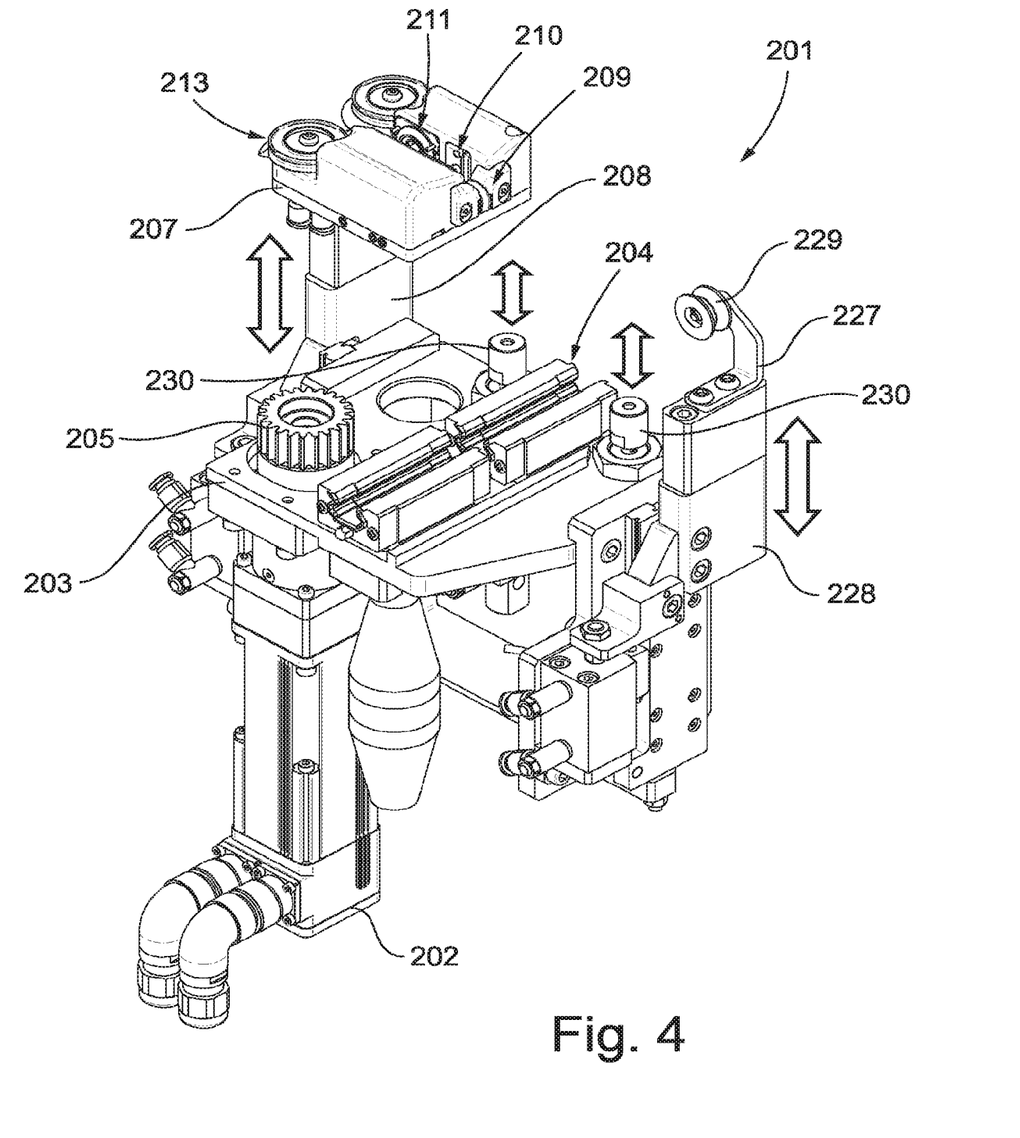
FIG. 4 is an axonometric view of a carriage of the loading module of FIG. 1.

Each carriage 201 is provided with at least one operating group selected from the group comprising: a cutting group, a braking group, a guiding-return group and a suction group of a textile sample; such at least one operating group is arranged at the side of the gripping members 200 facing towards the measurement modules 103, 104, 106.

Each carriage 201 is also provided with at least one auxiliary operating group selected from the group comprising: a guiding-return group and a braking group; such at least one auxiliary operating group is arranged at the side of the gripping members 200 opposite the one facing towards the measurement modules 103, 104 and 106.

Each carriage 201 is then coupled with own motor means 202 that actuate the translation movement thereof; the central unit is adapted to control and operate the motor means 202 for controlling and operating the movement of the respective carriage 201 so as to selectively arrange it at one of the members 200.

In greater detail and with particular reference to the embodiment represented in the attached figures, each carriage 201 comprises a base body 203 that is guided, by means of a rectilinear guide 204, in translation in both senses along a direction parallel to the loading direction DC.

The base body 203 is associated with the respective motor means 202 by means of means for transforming the rotary movement of the first into translation movement of the second, for example of the pinion 205 and rack 206 type, wherein the person skilled in the art will immediately understand that the motor means 202 and/or the means for transforming and transmitting the movement can have different and totally equivalent embodiments.

The base body 203 supports at least one first support body 207 that is arranged at the side of the gripping members 200 facing towards the measurement modules 103, 104, 106 and that supports at least one operating group selected from a cutting group, a braking group, a suction group and a return group of a textile sample.

The first support body 207 is supported by the base body 203 in a movable manner in a direction orthogonal to the sliding plane of the carriage 201 (i.e. along the axis X); a first linear actuator 208 is also supported by the base body 203 to drive the movement of the first support body 207 towards or away from the sliding plane of the carriage 201 (plane ZY) so as to be able to align the operating groups supported by the first support body 207 at the height, with respect to the plane ZY, of the textile sample to be picked up and to detach the textile sample from the respective gripping members so as to avoid sliding friction of the first on the second friction, which would alter and damage the textile sample, for example increasing the hairiness thereof or reducing the mechanical strength thereof.

Figure 5:
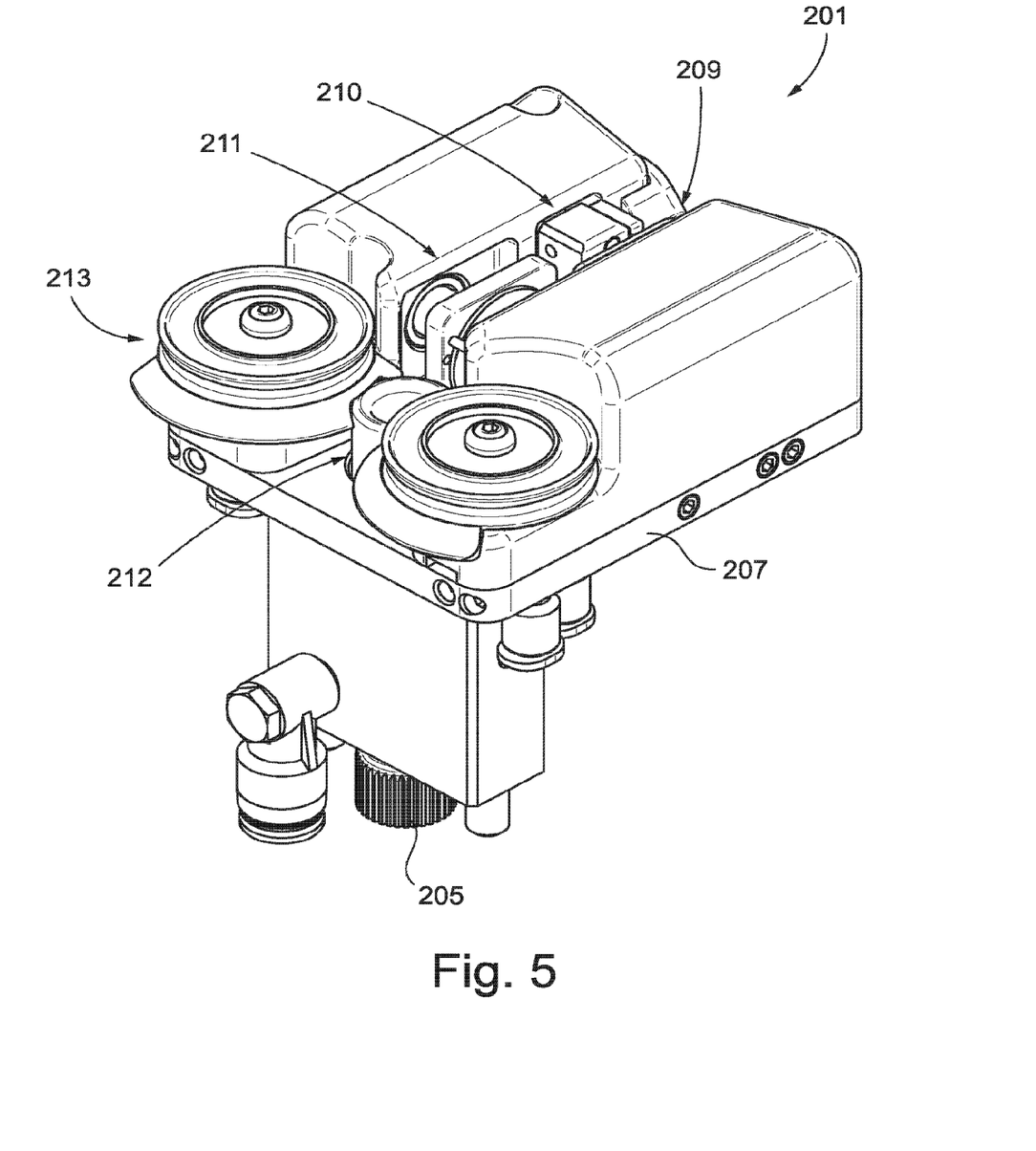
FIG. 5 is an axonometric view of a detail of the carriage of FIG. 4.
Figure 6:
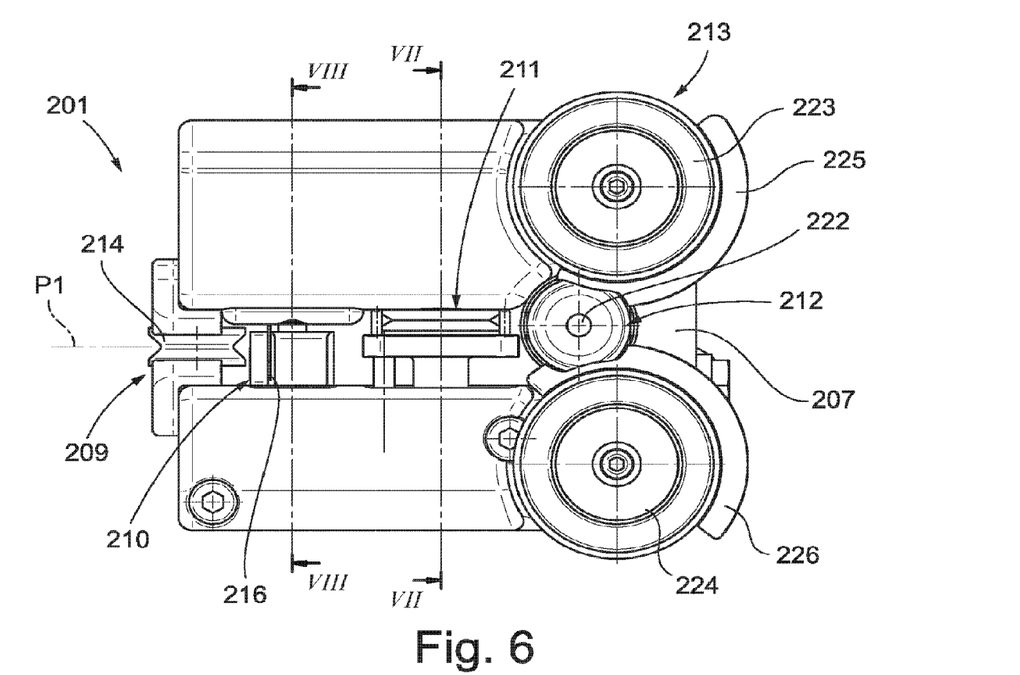
FIG. 6 is a front view of FIG. 5.

The first support body 207 supports, in succession starting from the inlet end (i.e. the end facing towards the gripping members) towards the outlet end (i.e. the end facing towards the measurement modules) along a sliding path P1 of the entering textile sample: a first guiding-return group 209, a cutting group 210, a braking group 211, a suction group 212 and a second guiding-return group 213.

The first guiding-return group 209 comprises a wheel or a roller 214 of the grooved type that is supported in a rotating manner by means of a shaft by the first support body 207; the roller 214 is arranged with its rotation axis parallel to the loading direction DC.

Figure 7:
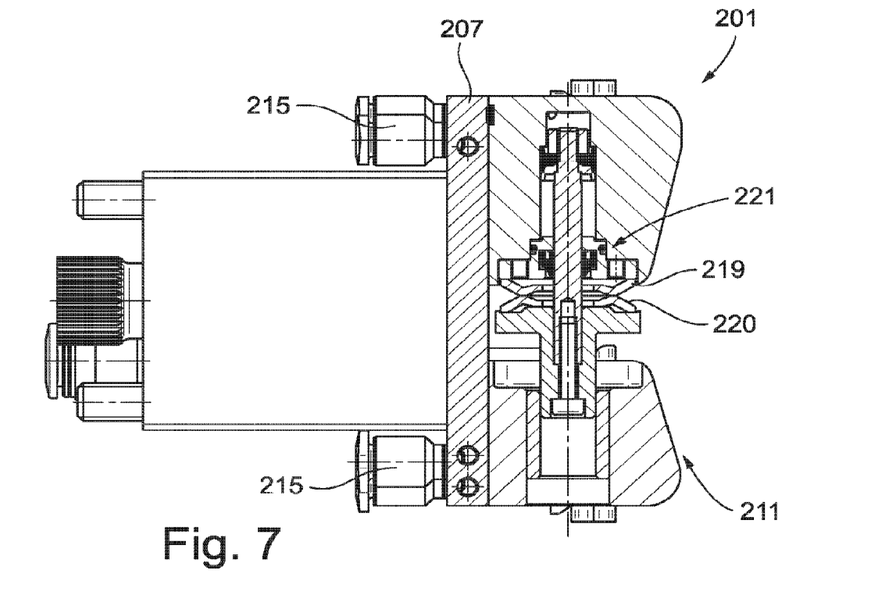
FIGS. 7 and 8 are sections, respectively according to the planes VII-VII and VIII-VIII of FIG. 6.

The cutting group 210 comprises a blade 216 and an abutment plate 217, one relatively movable towards and away from each other by means of a respective linear actuator 218 of the double-acting pneumatic cylinder-piston type.

Figure 8:
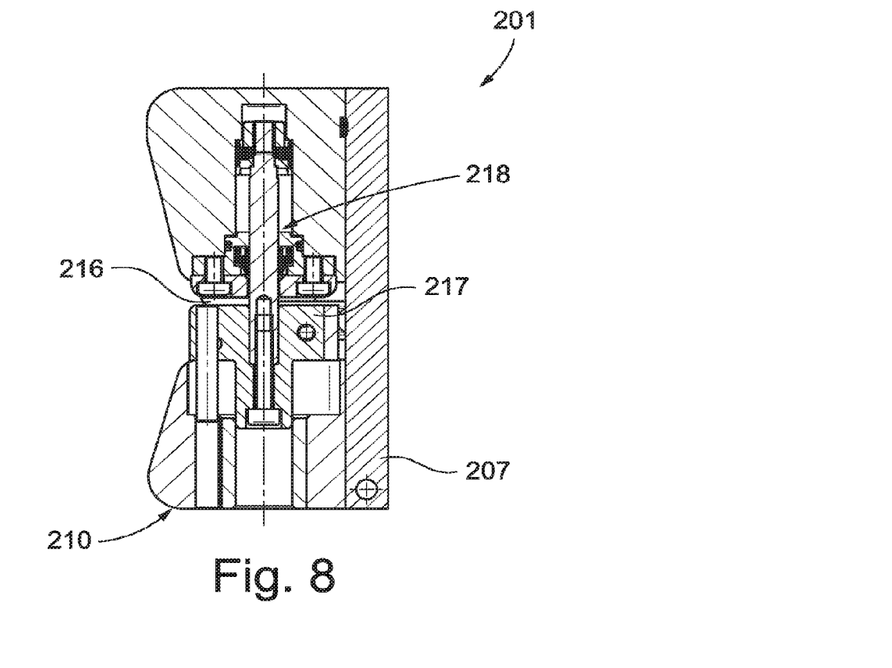

The braking group 211 comprises a pair of yarn-braking discs 219, 220 one of which is relatively movable towards and away from the other by means of a respective linear actuator 221 of the double-acting pneumatic cylinder-piston type.

The suction group 212 comprises a suction mouth 222 that is connected to a Venturimeter suction device, which is not shown since it is of the known type.

The second guiding-return group 213 comprises a pair of wheels 223 and 224 that are mounted in a rotating manner about a respective axis orthogonal to the plane ZY; along an arc of circumference of each of the two wheels 223 and 224 facing towards the measurement modules a profile 225 and 226 is arranged for directing the textile sample towards the measurement modules.

The fittings 215 to a pneumatic circuit are also provided on the first support body 207.

Advantageously, the base body 203 of each carriage 201 also supports a second support body 227 that is arranged at the side of the gripping members 200 facing towards the supply (creel) of the textile samples and that supports at least one auxiliary operating group selected from a braking group and a guiding-return group of the textile sample.

In the embodiment shown, the second support body 227 is coupled to the base body 203 in a movable manner in a direction orthogonal to the sliding plane of the carriage 201 (i.e. axis X); a second linear actuator 228 is also supported by the base body 203 in order to drive the movement of the second support body 227 towards and away from the sliding plane of the carriage 201 (plane ZY) so as to be able to modify the height of the auxiliary operating groups supported by the second support body 226 with respect to the height with respect to the plane ZY of the textile sample to be picked up and to detach the textile sample from the respective gripping members so as to avoid sliding friction of the first on the second friction, which would alter and damage the textile sample, for example increasing the hairiness thereof or reducing the mechanical strength thereof. The second support body 227 supports a braking group and/or guiding-return group consisting of a wheel 229, advantageously of the grooved type, rotatable about a vertical axis (axis Z, parallel to the sliding direction DC); by changing the height of the wheel 229 with respect to the sliding plane of the carriage 201, the inlet trajectory of the textile sample and the resistance to the sliding exerted on it are changed.

Each carriage 201 also comprises actuator means 230 for actuating the gripping members 200 between their locking position and their unlocking position.

Figure 9:
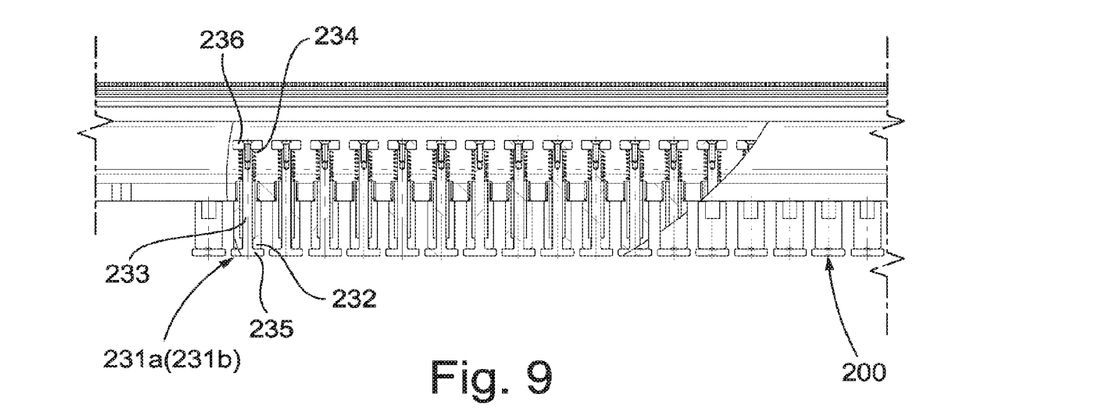
FIG. 9 shows a partial section view of the gripping members of the loading module of the equipment of FIG. 1.

Each gripping member 200, in fact, comprises a pair of grippers 231a, 231b aligned with each other along a direction coplanar and orthogonal to the loading direction DC for gripping two corresponding portions of the inlet end of a respective textile sample.

Each gripper 231a, 231b comprises a first element 232 that is fixed with respect to the housing 201 and a second element 233 that is coupled to the first element 232 in a movable manner in contrast to elastic means 234 between a close position, for picking up and locking the respective portion of the inlet end of the respective textile sample between them, and a spaced position, for releasing and unlocking the respective portion of the inlet end of the respective textile sample.

In the embodiment represented in the attached figures, the first element 232 consists of a hollow pin and the second element 233 consists of a stem inserted in a movable manner in the first element 232 and provided at one end with a head 235 that rests on a corresponding end of the hollow pin and at the opposite end with an abutment 236 of the elastic means 234.

The textile sample is clamped between the head 235 and the hollow pin.

The actuator means 230 comprise a pair of thrusting shafts pneumatically driven adapted to act on the second elements 233 of each pair of grippers 231a, 231b in contrast to the elastic means 234 in order to force them in their unlocking and release position.

The measurement modules, the loading module and the handling means are equipped with an own microprocessor connected to the central unit, which makes the equipment 100 of the modular type assemblable as a function of different requirements.

For the person skilled in the art the operation of the equipment 100 can be immediately understood from the above description and the attached figures.

An operator manually arranges the inlet ends of the samples to be tested between the pairs of grippers 231a, 231b of the gripping members 200.

The central unit, according to what is pre-set and programmed, controls and operates the various components of the equipment 100 to carry out one or more tests on the textile samples loaded.

As a function of which textile sample must be tested, one of the two carriages 201 positions beside the respective pair of grippers 231a, 231b that holds the respective inlet end thereof. The first support body 207 and the second support body 227 are arranged at the desired height with respect to the sliding plane of the respective carriage 201. The handling means 105 are arranged with the gripping head at the inlet end of the textile sample to be picked up and pick it up as soon as it is released by the respective pair of grippers 231a, 231b, in turn pushed in their unlocking and release position by the actuator means 230 supported by the carriage 201.

The handling means 105 arrange the end of the textile sample thus picked up at the inlet to the operating groups supported by the first support body 207 of the carriage 201 pulling it along the path P1 and subsequently insert it into the pre-set measurement module 103, 104 or 106, which then carries out the respective test once or more times according to what is programmed.

While the test is being carried out, the textile sample is hold in position detached from the respective pair of grippers, is guided and supported by the first guiding-return group 209 and by the second guiding-return group 213 and possibly braked by the braking group 212 of the respective carriage 201.

While a textile sample is tested by one of the measurement modules 103, 104 and 106, another textile sample can be simultaneously tested in another of the measurement modules 103, 104 and 106. The measurements can thus take place even in parallel on different measurement modules. Similarly, it is possible to carry out a test on a rove by means of the fourth measurement module 107 simultaneously and in parallel to the tests carried out on one or two textile samples by means of one of the measurement modules 103, 104 and 106.

At the end of the tests, where necessary, the textile sample is cut by the cutting group 210 of the respective carriage 201. The suction group 212, along with the suction groups that are provided locally at the single measurement modules, remove the portions of the textile sample thus cut or in any case separated, without the need of the intervention of the handling means 105.

It is noted that the carriages 201 can be arranged selectively beside any one of the gripping members 200 and that the two carriages 201 are independent from each other.

The equipment 100 is complete with safety barriers, for example of the photocell type.

The equipment object of the present invention has the advantage of allowing managing in a simple, quick and flexible manner the picking up of one or more textile samples and their feeding to the measurement modules which it is equipped with.

The equipment object of the present invention has the advantage of supporting and guiding the textile samples being tested so as to avoid undesired friction and pre-loads. This allows avoiding the textile samples from being altered or damaged and allows obtaining more accurate and precise measurements.

The equipment object of the present invention has the advantage of managing in a quick and simple manner the removal of the textile samples already tested without using handling means.

The equipment thus conceived can undergo numerous modifications and variants, all of which are covered by the invention; moreover, all of the details can be replaced by technically equivalent elements. In practice, the materials used, as well as the sizes, can be whatever according to the technical needs.

The invention claimed is:

1. Modular equipment for automatically determining features of elongated textile samples, comprising:
   a housing on which at least one loading module for loading inlet ends of a plurality of textile samples to be tested is mounted, each textile sample being fed from a corresponding package supported by support means that are associable with said equipment,
   at least one measurement module for measuring at least one structural or physical-mechanical feature of said textile samples,
   handling means for handling said textile samples between said loading module and said at least one measurement module, and
   a central unit of the programmable type for controlling and managing said loading module, said at least one measurement module, and said handling means,
   wherein said loading module comprises:
      a plurality of gripping members that are arranged aligned to one another along a loading direction, wherein each of said gripping members is movable between a gripping position and a release position of the inlet end of a respective textile sample,
   at least one carriage that is driven in a movable manner in both translation senses along a translation direction parallel to said loading direction, and
   motor means associated with said at least one carriage for operating said at least one carriage moving along said translation direction,
   wherein said at least one carriage comprises at least one operating group selected from the group comprising: a cutting group, a braking group, a guiding-return group, and a suction group for a textile sample, said at least one operating group is arranged at a side of said gripping members facing towards said at least one measurement module, and
   wherein said central unit is adapted to control and operate said motor means for controlling and operating the movement of said at least one carriage so as to selectively arrange said at least one carriage at one of said gripping members.

2. The equipment according to claim 1, wherein said at least one carriage comprises at least one auxiliary operating group selected from the group comprising an auxiliary guiding-return group and an auxiliary braking group of the inlet end of a textile sample, wherein said at least one auxiliary group is arranged at a side of said gripping members opposite that facing towards said at least one measurement module.

3. The equipment according to claim 1, wherein said at least one carriage comprises a first support body that is arranged at the side of said gripping members facing towards said at least one measurement module and that supports in succession a cutting group, a braking group, a suction group, and a guiding-return group, wherein said central unit is adapted to control said cutting, braking and suction groups.

4. The equipment according to claim 3, wherein said first support body supports at least one first inlet wheel that is supported in a rotating manner and that is arranged upstream of said cutting, braking, suction, and guiding-return groups.

5. The equipment according to claim 2, wherein said at least one carriage comprises a second support body that is arranged at the side of said gripping members opposite the one facing towards said at least one measurement module and that supports an auxiliary guiding-return group of the inlet end of a textile sample.

6. The equipment according to claim 1, wherein said at least one carriage comprises actuator means for actuating said gripping members said actuator means being controlled by said central unit for actuating said gripping members between the gripping position and the release position.

7. The equipment according to claim 1, wherein said loading module comprises at least one pair of said carriages.

8. The equipment according to claim 1, further comprising at least one first measurement module for measuring at least one structural feature of said textile samples and at least one second measurement module for determining at least one physical-mechanical feature of said textile samples, wherein said first measurement module and said second measurement module are configured to operate simultaneously on a same or on different textile samples.

9. The equipment according to claim 8, wherein said first measurement module is configured for measuring at least one of hairiness and evenness of linear mass of said textile samples, and said at least one second measurement module is configured for measuring at least one dynamometric feature of said textile samples.

10. The equipment according to claim 8, further comprising at least one third measurement module for measuring a further structural feature of said textile samples.

11. The equipment according to claim 10, wherein said at least one third measurement module is configured for measuring linear mass of said textile samples.

12. The equipment according to claim 11, wherein said at least one first measurement module and said at least one third measurement module are arranged substantially aligned to one another along a sliding path of a textile sample at a first measuring area defined in said housing, and wherein said at least one second measurement module is arranged at a second measurement area defined in said housing and different from said first measurement area.

* * * * *